(12) United States Patent
Knight

(10) Patent No.: US 8,685,483 B2
(45) Date of Patent: Apr. 1, 2014

(54) ELECTROLYTE FORMULATION AND METHODS OF USE THEREOF TO TREAT DEHYDRATION

(76) Inventor: Philip M. Knight, Pike Road, AL (US)

( * ) Notice: Subject to any disclaimer, the term of this patent is extended or adjusted under 35 U.S.C. 154(b) by 317 days.

(21) Appl. No.: 13/209,887

(22) Filed: Aug. 15, 2011

(65) Prior Publication Data

US 2013/0045297 A1    Feb. 21, 2013

Related U.S. Application Data

(60) Provisional application No. 61/373,443, filed on Aug. 13, 2010.

(51) Int. Cl.
*A23L 1/304* (2006.01)

(52) U.S. Cl.
USPC ............. 426/573; 426/74; 426/548; 426/590; 426/648

(58) Field of Classification Search
CPC .. A23L 2/38; A23V 2200/16; A23V 2200/33; A23V 2250/1578
USPC .................................... 426/74, 548, 590, 648
See application file for complete search history.

(56) References Cited

U.S. PATENT DOCUMENTS

2007/0259054 A1 * 11/2007 Ayala ........................... 424/679

OTHER PUBLICATIONS

Thomas et.al.,"Physician Misdiagnosis of Dehydration in Older Adults," Journal of the American Medical Directors Assoc.4(5):251-254(2003).
Mourad et.al.,"Role of Nitric Oxide in Intestinal Water and Electrolyte Transport," Gut 44:143-147(1999).
Rehman et.al.,"Modulation of Small Intestinal Nitric Oxide Synthase by Gum Arabic," Experimental Biology and Medicine 229:895-901(2004).
Leiper, "Intestinal Water Absorption-Implications for the Formulation of Rehydration Solutions," Int. J. Sports Med. Suppl. 19: S129-32(1998).
Hunt et.al.,"Effect of Meal Volume and Energy Density on the Gastric Emptying of Carbohydrates," Gastroenterology 89:1326-1330(1985).

* cited by examiner

*Primary Examiner* — Helen F Heggestad

(57) ABSTRACT

This invention relates to electrolyte formulations and methods of use thereof to treat or prevent dehydration and taste fatigue. The electrolyte formulation of the invention addresses the needs of a broad population, particularly the needs of an older population. The electrolyte formulation of this invention comprises a dietary fiber source, such as *Acacia* Gum, a sodium ion source, a potassium ion source, a calcium ion source, a chloride ion source, and a citrate ion source.

80 Claims, No Drawings

ELECTROLYTE FORMULATION AND METHODS OF USE THEREOF TO TREAT DEHYDRATION

FIELD OF THE INVENTION

This invention relates to electrolyte formulations and methods of use thereof to treat or prevent dehydration and taste fatigue.

BACKGROUND

Dehydration can have serious effects, including headaches, muscle cramps, confusion, hypotension, dizziness or fainting, and can generally result in delirium, unconsciousness, swelling of the tongue and in extreme cases death, without appropriate treatment.

Dehydration can occur at any age. However, dehydration is particularly common among older people. Many senior citizens suffer from symptoms of dehydration. According to the Health Care Financing Administration, dehydration of geriatric patient is a frequent cause of hospitilization and is one of the ten most frequent admitting diagnoses for Medicare hospitilizations. Dehydration of geriatric patient is caused by many reasons. Two of the most evident reasons are the decline in the geriatric patient's ability to sense a need to imbibe fluids and the actual decline in the fluid intake. In people over age 50, the body's thirst sensation diminishes and continues diminishing with age. Moreover, dehydration is a difficult clinical diagnosis in older people because the physical sign of dehydration are often confusing. See Thomas et al., "Physician Misdiagnosis of Dehydration in Older Adult," Journal of the American Medical Directors Association 4(5): 251-254 (2003). In fact, dehydration prevention has become one of the major clinical, quality care indicators in nursing homes.

Dehydration, despite the name, does not simply mean loss of water. Dehydration is excessive loss of body fluid: water and solutes (e.g., electrolytes) are usually lost in roughly equal quantities to how they exist in blood plasma. Treatment or prevention of dehydration usually involves the intake of necessary water and electrolytes. A number of beverages and concentrated beverage compositions are currently available (including liquid, powdered or tablet concentrates) for rehydration of fluids lost during exercise or vigorous activity. These rehydration beverages (also known as "sports drinks"), available in both ready-to-drink form as well as those prepared by the user, may be consumed before, during and after exercise. While these sports drinks rehydrate the body better than plain water, these sports beverage generally target the robust, active and healthy portion of a society.

For geriatric patients, however, the treatment or prevention of dehydration may not be easily accomplishable, due in part to the change of physiological condition of the geriatric patients. Geriatric patients are generally less motivated to eat and drink compared to a younger, healthier population, leaving to declined physiologic parameters (e.g., declined blood-electrolyte level) in the body. As these physiologic parameters decline, the lack of a desire to hydrate and feed for the geriatric patents becomes even more pronounced. These factors contribute to a negative cycle for geriatric patients for effective treatment or prevention of dehydration. Therefore, what is needed in the art is an electrolyte formulation that can be administered to geriatric patients to prevent dehydration while also reducing taste fatigue. This invention answers that need.

SUMMARY OF THE INVENTION

One aspect of the invention relates to an electrolyte formulation comprising *Acacia* Gum, a sodium ion source, a potassium ion source, a calcium ion source, a chloride ion source, and a citrate ion source.

In one embodiment, the invention relates to a liquid electrolyte formulation. The liquid electrolyte formulation comprises about 0.05 wt % to about 10 wt % *Acacia* Gum (Gum Arabic), about 0.08 wt % to about 0.5 wt % calcium chloride, about 0.1 wt % to about 1.0 wt % sodium citrate, about 0.02 wt % to about 0.1 wt % tri-potassium citrate monohydrate, less than about 0.25 wt % potassium chloride, less than about 1.2 wt % sodium chloride, and water. The *Acacia* Gum in the liquid electrolyte formulation is present in sufficient amounts to increase the absorption of water by modulating intestinal activity. The liquid electrolyte formulation electrolyte formulation has a pH ranging from about 3.9 to about 4.2, and contains sufficiently low amounts of sodium chloride and potassium chloride to reduce the saline and/or bitter taste while maintaining an effective amount of chloride, sodium, potassium, and calcium ions in the electrolyte formulation.

In another embodiment, the invention relates to a powder electrolyte composition for reconstitution in water. The powder electrolyte composition comprises about 0.5 wt % to about 75 wt % *Acacia* Gum (Gum Arabic), about 0.6 wt % to about 6 wt % calcium chloride, about 2 wt % to about 18 wt % sodium citrate, about 0.4 wt % to about 4 wt % tri-potassium citrate monohydrate, less than about 6 wt % potassium chloride, and less than about 3 wt % sodium chloride. Upon reconstitution of the powder composition in water, the *Acacia* Gum is present in sufficient amounts to increase the absorption of water by modulating intestinal activity. The powder electrolyte composition, upon reconstitution in water, has a pH ranging from about 3.9 to about 4.2, and contains sufficiently low amounts of sodium chloride and potassium chloride to reduce the saline and/or bitter taste while maintaining an effective amount of chloride, sodium, potassium, and calcium ions in the electrolyte composition.

In another embodiment, the invention relates to a tablet electrolyte composition for reconstitution in water. The tablet electrolyte composition comprises about 0.5 wt % to about 75 wt % *Acacia* Gum (Gum Arabic), about 0.1 to about 8 wt % tri-calcium citrate, about 2 wt % to about 18 wt % sodium citrate, about 0.4 wt % to about 4 wt % tri-potassium citrate monohydrate, less than about 6 wt % potassium chloride, and less than about 3 wt % sodium chloride. Upon reconstitution of the tablet electrolyte composition in water, the *Acacia* Gum is present in sufficient amounts to increase the absorption of water by modulating intestinal activity. The tablet electrolyte composition, upon reconstitution in water, has a pH ranging from about 3.9 to about 4.2, and contains sufficiently low amounts of sodium chloride and potassium chloride to reduce the saline and/or bitter taste while maintaining an effective amount of chloride, sodium, potassium, and calcium ions in the electrolyte composition.

In another embodiment, the invention relates to a method of reducing or preventing taste fatigue of a subject consuming an electrolyte formulation. The method comprises the step of administering to a subject an electrolyte formulation comprising *Acacia* Gum, calcium chloride or tri-calcium citrate, sodium citrate, tri-potassium citrate monohydrate, potassium chloride, and sodium chloride. The electrolyte formulation administered contains sufficiently low amounts of sodium chloride and potassium chloride to reduce the saline and/or bitter taste while maintaining an effective amount of chloride, sodium, potassium, and calcium ions in the electrolyte formulation, thereby reducing or preventing taste fatigue of the subject consuming the electrolyte formulation.

In another embodiment, the invention relates to a method for treating or preventing dehydration. The method comprises the step of administering to a subject in need thereof an electrolyte formulation comprising *Acacia* Gum, calcium chloride or tri-calcium citrate, sodium citrate, tri-potassium citrate monohydrate, potassium chloride, and sodium chloride. The *Acacia* Gum in the electrolyte formulation is present in sufficient amounts to increase the absorption of water by modulating intestinal activity, thereby treating or preventing dehydration of the subject.

In another aspect of the invention, the *Acacia* Gum in the electrolyte formulation can be replaced by any dietary fiber source known to one skilled in the art. Alternatively, a dietary fiber source may be added to the electrolyte formulation in addition to the *Acacia* Gum. The dietary fiber used in the electrolyte formulation may include a mixture of dietary fiber sources.

DETAILED DESCRIPTION

This invention relates to electrolyte formulations and methods of use thereof to treat or prevent dehydration and taste fatigue. The electrolyte formulation of the invention addresses the needs of a broad population, particularly the needs of an older population.

One aspect of the invention relates to an electrolyte formulation comprising *Acacia* Gum, a sodium ion source, a potassium ion source, a calcium ion source, a chloride ion source, and a citrate ion source. In some embodiments, the electrolyte formulation of this invention comprises *Acacia* Gum, calcium chloride or tri-calcium citrate, sodium citrate, tri-potassium citrate monohydrate, potassium chloride, and sodium chloride.

*Acacia* Gum (or Gum *Acacia*, Gum arabic) is a complex mixture of polysaccharides and glycoproteins. *Acacia* Gum is a soluble fiber and is a negatively charged natural product with moderate emulsifying properties. It has been used in the food industry primarily as a stabilizer, or sometimes used as an emulsifying agent, suspending or viscosity increasing agent.

*Acacia* gum may be employed in the electrolyte formulation to aid in the absorption of water, electrolytes and carbohydrate. Nutrient and electrolyte absorption is regulated by multiple mechanisms at the cellular and molecular levels. The small intestine is the major site of nutrient and electrolyte absorption in the gastrointestinal tract. Nitric oxide (NO) metabolism plays a critical role in the regulation of intestinal function. NO is a gas that also has the properties of a free radical and that is generated from L-arginine (Arg) by an enzyme, NO synthase (NOS). It has been shown that NO alters intestinal muscular contractility and motility, as well as water and electrolyte absorption and secretion through modulation of mucosal cGMP and cAMP levels. See Mourad et al., "Role of nitric oxide in intestinal water and electrolyte transport," Gut 44:143-147 (1999).

Both in vivo and in vitro results using a glucose-electrolyte solution in rat jejunal perfusions show that *Acacia* gum has the ability of scavenging chemically generated NO diffused into the intestinal lumen, as well as partially inhibiting NOS and thus modulating intestinal absorption through these mechanisms. See Rehman et al, "Modulation of Small Intestinal Nitric Oxide Synthase by Gum Arabic," Experimental Biology and Medicine 229: 895-901 (2004). Thus, presence of *Acacia* gum may aid in water, electrolyte and carbohydrate absorption by modulating intestinal activity. Additionally, the presence of *Acacia* gum in the electrolyte formulation aids in increasing the mass/volume of the stool and increasing the retention time of electrolyte, water and carbohydrate in the intestine, which result in an increased absorption of the water, electrolyte and carbohydrate. It is believed that the presence of *Acacia* gum improves the absorption of electrolytes in both the normal and stressed intestine by as much as 40%.

Any source of sodium ion known to those skilled in the art can be used in the invention. Examples of useful sodium ion sources include, but are not limited to, sodium chloride, sodium citrate, sodium benzoate, sodium carboxymethylcellulose (CMC gum), sodium bicarbonate, sodium lactate, sodium pyruvate, sodium acetate and combinations thereof. The sodium ion content of the electrolyte formulation, in a liquid/beverage form or as reconstituted in water/liquid, may be about 5 mEq/L or more (mEq refers to milliequivalents). For instance, the sodium ion content may range from about 5 to about 100 mEq/L, from about 10 to about 75 mEq/L, from about 30 to about 60 mEq/L, or from about 40 to about 50 mEq/L. This sodium concentration indicates the total amount of sodium ion present in the liquid or beverage electrolyte formulation.

Any source of potassium ion known to those skilled in the art can be used in the invention. Examples of useful potassium ion sources include, but are not limited to, potassium chloride, tripotassium citrate monohydrate, potassium sorbate, potassium monophosphate, potassium diphosphate, and combinations thereof. The potassium ion content of the electrolyte formulation, in a liquid/beverage form or as reconstituted in water/liquid, may be about 4 mEq/L or more. For instance, the potassium ion content may range from about 4 to about 45 mEq/L, from about 8 to about 30 mEq/L, or from about 10 to about 25 mEq/L. The presence of a sufficient level of potassium in an electrolyte formulation may provide nutritional benefits in addition to the hydration benefits. For example, potassium deficiency (hypokalemia), which may be caused by diarrhea and vomiting, may result in cardiovascular irregularities or muscular cramping. The presence of potassium at a concentration more than about 20 meq/L may contribute to the alleviation of hypokalemia and/or its symptoms.

The calcium ion used in the invention may come from a variety of sources known to those skilled in the art. Examples of useful calcium ion source include, but are not limited to, calcium chloride, calcium citrate, calcium lactate, calcium carbonate, calcium phosphate salts, and combinations thereof. The calcium ion content of the electrolyte formulation, in a liquid/beverage form or as reconstituted in water/liquid, may be about 1 mEq/L or more. For instance, the calcium ion content may range from about 5 to about 60 mEq/L, from about 10 to about 50 mEq/L, or from about 30 to about 40 mEq/L.

The chloride ion used in the invention can come from various sources known to those skilled in the art. Examples of useful chloride sources include, but are not limited to, sodium chloride, potassium chloride, calcium chloride, magnesium chloride and combinations thereof. The chloride ion content of the electrolyte formulation, in a liquid/beverage form or as reconstituted in water/liquid, may be about 10 mEq/L or more. For instance, the chloride ion content may range from about 10 to about 60 mEq/L, or from about 11 to about 35 mEq/L.

The electrolyte formulation of the invention may also comprise a citrate source, a magnesium source, a zinc source and/or a carbohydrate source. Examples of citrate sources include, but are not limited to, citric acid, sodium citrate, calcium citrate, potassium citrate monohydrate, and combinations thereof. Increasing the level of citric acid may provide taste benefits. The concentration of citrate may range, for instance, from about 10 to about 60 mEq/L, from about 15 to about 50 mEq/L, or from about 25 to about 35 mEq/L.

Examples of magnesium ion sources include, but are not limited to, magnesium oxide, magnesium acetate, magnesium chloride, magnesium citrate, magnesium carbonate, magnesium diphosphate, magnesium triphosphate, magnesium in the form of an amino acid and combinations thereof. If present, the concentration of magnesium may be from about 0.5 to about 20 mEq/L, from about 0.5 to about 6 mEq/L, or from about 1 to about 3 mEq/L.

It has been reported that the presence of zinc in an electrolyte formulation may help replace zinc that has been lost due to diarrhea and/or vomiting, and may help reduce the severity and/or duration of diarrhea. Presence of zinc in electrolyte formulation may also assist in enhancing the absorption of water, electrolyte and/or carbohydrate in small intestine. Examples of zinc source include zinc gluconate, zinc sulfate, zinc chloride, zinc citrate, zinc bicarbonate, zinc carbonate, zinc hydroxide, zinc lactate, zinc acetate, zinc fluoride, zinc bromide, zinc sulfonate and combinations thereof. If present, the concentration of zinc may be from about 0.3 to about 100 mEq/L, from about 0.6 to about 5 mEq/L, from about 0.6 to about 3 mEq/L, or from about 0.6 to about 1.2 mEq/L.

Addition of a carbohydrate source in the electrolyte formulation may be desirable, particularly for individuals who seek for additional energy source in an electrolyte formulation. Carbohydrate may also help enhance the absorption of water and electrolyte in the electrolyte formulation. For example, glucose may enhance water and sodium absorption from the intestines into the bloodstream. See Leiper, "Intestinal water absorption—implications for the formulation of rehydration solutions," hit. J. Sports Med. Suppl. 19: S129-32 (1998). Carbohydrates in fluid replacement have two divergent effects in the digestive system. Initially, carbohydrates in fluids will slow gastric emptying, and these same carbohydrate fluids will be rapidly absorbed in the small intestine. See Hunt et al., "Effect of meal volume and energy density on the gastric emptying of carbohydrates," Gastroenterology 89:1326-1330 (1985). There is a net gain in rate of overall uptake of water and electrolytes attributed to the small intestines with the increased concentration of carbohydrate in the fluids.

Any sugar known to those skilled in the art can be used as the carbohydrate sources, including but not limited to, glucose (or dextrose), fructose, sucrose, maltose, maltodextrin, galactose, trehalose, fructo-oligosaccharides, beta-glucan, trioses such as pyruvate and lactate, and combinations thereof. If present, the concentration of carbohydrate may be present from about 5 to about 60 grams/L, for instance, from about 20 to about 50 grams/L, or from about 25 to about 35 grams/L. In addition, other carbohydrate sources, not necessary prepared in the electrolyte formulation, such as food that is rich in starch (such as cereals, bread and pasta), may be administered in combination with the administration of the electrolyte formulation or separately to further aid in absorption of water and electrolytes.

Sugar substitutes can also be used in the electrolyte formulation. Sugar substitutes can be desirable for flavoring and/or for maintaining a low caloric level of the electrolyte formulation. In addition, they may have beneficial effects for certain patients, such as for patients with diabetes mellitus and/or tooth decay. Suitable sugar substitutes include, but are not limited to sucralose, saccharin, aspartame, neotame, acesulfame potassium, stevia and combinations thereof. Using suitable sugar substitutes, the caloric intake of the electrolyte formulation can be controlled to less than about 200 calories per liter, less than about 150 calories per liter, or less than about 100 calories per liter.

Addition of one or more vitamins in the electrolyte formulation may be desirable, particularly for individuals who seek for additional benefits vitamins may bring to an electrolyte formulation. For example, B vitamins (e.g., vitamin B1, vitamin B2, vitamin B3, vitamin B5, vitamin B6, vitamin B7, vitamin B9, vitamin B12, etc.) play an important role in cell metabolism and addition of these vitamins can assist in increasing the rate of metabolism and enhancing immune and nervous system functions and the like, for instance, vitamin B3 and/or its amide salt (e.g, niacinamide) may be added in the electrolyte formulation to assist in treating insomnia, alcohol-induced dehydration, e.g., hangover, and the like. Examples of vitamins that may be present include choline, vitamin B1 (thiamin), vitamin B2 (riboflavin), vitamin B3 (niacin and its amide such as niacinamide), vitamin B5 (pantothenic acid), vitamin B6, vitamin B7 (biotin), vitamin B9 (folic acid or folate), vitamin B12, vitamin A, vitamin C, vitamin D, vitamin E, vitamin K, and combinations thereof. If present, a vitamin may have a concentration in an electrolyte formulation sufficient to provide from 5% to 100% or more of the recommended daily value. For example, an electrolyte formulation including B vitamins and/or vitamin C may contain more than 100% of the recommended daily value, for example 200%, 300% or 500% of the recommended daily value.

One or more dietary supplements may be present in the electrolyte formulation. Examples of dietary supplements that may be present include minerals, such as iron, phosphorus, iodine, magnesium, selenium, copper, manganese, chromium, molybdenum, nickel, tin, silicon, vanadium and boron; antioxidants, such as carotene, eugenol, lutein, lycopene, and flavonoids; glucosamine; glycosaminoglycans, such as chondroitin and hyaluronic acid; probiotics, such as *Lactobacillus reuteri* and *Lactobacillus acidophilus*; herbal extracts; and combinations thereof. If present, a dietary supplement may have a concentration in an electrolyte formulation sufficient to provide from 5% to 100% of the recommended daily value.

Food additives can also be used in the electrolyte formulation. Food additives may function to preserve flavor or improve its taste and appearance, or as preservative to inhibit the growth of bacteria, fungi and mold, and to provide a longer shelf life. Suitable food additives include, but are not limited to, sodium benzoate, potassium sorbate, citric acid monohydrate, calcium propionate, sodium nitrate, sodium nitrite, sulfites (sulfur dioxide, sodium bisulfite, potassium hydrogen sulfite, etc.), disodium EDTA, and combinations thereof.

In addition, flavoring agents and flavoring-enhancer agents may also be used in the electrolyte formulation. Suitable flavoring agents include, but are not limited to, anise oil, cinnamon oil, vanilla, vanillin, cocoa, chocolate, menthol, grape, cola, root beer, peppermint oil, oil of wintergreen, clove oil, bay oil, anise oil, eucalyptus, thyme oil, cedar leaf oil, oil of nutmeg, oil of sage, oil of bitter almonds, cassia oil, citrus oils such as lemon, orange, lime and grapefruit oils, fruit punch, and fruit essences, including apple, orange (e.g., mandarin orange), lemonade, pear, peach, berry, wildberry, blueberry, kiwi, strawberry, raspberry, cherry, plum, pineapple, apricot, the like. These can be included by means of an artificial or natural flavor system and can be combined and varied to suit individual taste. Examples of suitable flavoring-enhancer agents include calcium chloride, magnesium chloride, sodium citrate, potassium citrate, tartaric and maleic acids and salts thereof, and combinations thereof.

The electrolyte formulation, whether in a liquid/beverage form or as reconstituted in water/liquid, has a pH ranging from about 3 to about 7, such as from about 3.3 to about 4.5, or from about 3.9 to about 4.2. The pH range is adjusted to keep the ingredients of the electrolyte formulation, such as preservatives, stable and effective. One way to adjust the pH of the electrolyte formulation is to maintain a certain citrate level, as known in the art. The pH is typically higher than 3, as acidic pH's below 3 may have a negative effect on the stability of the electrolyte formulation.

The electrolyte formulation can take many forms including, but not limited to, liquid, gel, dry powder, tablet or capsule. For instance, the liquid or beverage electrolyte formulation may be manufactured and sold as a drinkable beverage for directly oral administration by a subject. The electrolyte formulation may also be prepared in concentrated forms, such as a concentrated liquid, or a powder or tablet composition, to be diluted or reconstituted for use by addition of water or any other appropriate liquids. Such reconstitution is made with the requisite amounts of water/liquid to ensure that the beverage to be consumed contains the active components in effective amounts. The liquids or beverages to be added for reconsititution of the electrolyte formulation may also include liquid meal or drinks such as sports drink, which can further include electrolytes and/or carbohydrates. The concentrated electrolyte composition may also be solubilized in water/liquid/beverage and then brought to a frozen state, so as to provide—for example—flavored ices on sticks, like the ones known under the commercial name or trade mark "Popsicle®".

Liquid Electrolyte Formulation

The liquid or beverage electrolyte formulation includes sufficient amounts of *Acacia* gum to increase the absorption of water, and/or electrolyte including the ions described herein, and/or carbohydrate by modulating intestinal activity. The *Acacia* gum may be present in an amount from about 0.05 wt % to about 10 wt %, for instance, from about 0.06 wt % to about 8 wt %, from about 0.08 to about 4 wt %, from about 0.1 wt % to about 3.2 wt %, or from about 0.5 wt % to about 1.5 wt %.

The liquid or beverage electrolyte formulation comprises sodium citrate ranging from about 0.1 wt % to about 1 wt %, for instance, from about 0.2 wt % to about 0.5 wt %, or from about 0.3 wt % to about 0.4 wt %.

The liquid or beverage electrolyte formulation comprises tri-potassium citrate monohydrate ranging from about 0.02 wt % to about 0.10 wt %, for instance, from about 0.04 wt % to about 0.08 wt %.

To reduce the saline and/or bitter taste while maintaining an effective amount of chloride, sodium, potassium and calcium ions in the electrolyte formulation, the electrolyte formulation comprises sufficiently low amounts of sodium chloride. In one embodiment, the sodium chloride content of the electrolyte formulation may be about 1.2 wt % or less. For example, the sodium chloride content may range from about 0.01 wt % to about 1.2 wt %, or from about 0.01 wt % to about 0.6 wt %. In one embodiment, the formulation includes about 0.1 wt % or less sodium chloride. In another embodiment, the electrolyte formulation is free of sodium chloride.

For a similar reason, the electrolyte formulation also comprises sufficiently low amounts of potassium chloride. In one embodiment, the potassium chloride content of the electrolyte formulation may be about 0.25 wt % or less. For example, the potassium chloride content may range from about 0.05 wt % to about 0.25 wt %, or from about 0.05 wt % to about 0.12 wt %. In one embodiment, the formulation includes about 0.1 wt % or less potassium chloride.

The liquid or beverage electrolyte formulation may comprise calcium chloride ranging from about 0.08 wt % to about 0.5 wt %, for instance, from about 0.08 wt % to about 0.22 wt %, or from about 0.10 wt % to about 0.15 wt %. Addition of calcium chloride in the electrolyte formulation also allows for a significant reduction or complete elimination of sodium chloride (e.g., 50% to 100% reduction compared to the electrolyte formulations widely known on the market, e.g., Gatorade® and Pedialyte®) as well as reduction of potassium chloride in the liquid formulation, while still maintaining the recommended miliequivalents concentration of chloride ions. This reduction or elimination of sodium chloride and potassium chloride reduces of saltiness and/or bitterness taste resulting from them and render the electrolyte formula more palatable, which in turn stimulates the increased intake of the electrolyte formulation.

The liquid or beverage electrolyte formulation may comprise carbohydrate (e.g., sugars) ranging from about 0.7 wt % to about 20 wt %, for instance, from about 1.5 wt % to about 3.7 wt %. Suitable carbohydrates include, but are not limited to, dextrose, fructose, sucrose, maltose, maltodextrin, galactose, trehalose, fructo-oligosaccharides, beta-glucan, trioses, and combinations thereof. For example, a combination of about 0.6 wt % to about 15 wt % dextrose and about 0.1 wt % to about 5 wt % fructose may be present in the liquid formulation. In one embodiment, a combination of about 1.2 wt % to about 3.0 wt % dextrose and about 0.3 wt % to about 0.7 wt % fructose may be present in the liquid formulation. In another embodiment, a combination of about 1.3 wt % to about 2 wt % dextrose and about 0.4 wt % to about 0.6 wt % fructose may be present in the liquid formulation.

One or more sugar substitutes may be used in the liquid or beverage electrolyte formulation. Suitable sugar substitutes used in the liquid formulation include, for example, sucralose, saccharin, aspartame, acesulfame potassium, stevia, neotame and combinations thereof. Sugar substitutes, if present, may range from about 0.006 wt % to about 0.06 wt %, for instance, from about 0.006 wt % to about 0.03 wt %. For example, sucralose may be used in the liquid formulation ranging from about 0.006 wt % to about 0.06 wt %, or from about 0.006 wt % to about 0.03 wt %. In one embodiment, about 0.01 wt % to about 0.02 wt % sucralose may be used in the liquid formulation. With the appropriate amount of carbohydrate and sugar substitutes, the caloric intake of the liquid electrolyte formulation can be adjusted to less than about 150 calories per liter, for instance, less than about 100 calories per liter.

The liquid or beverage electrolyte formulation may further comprise preservatives, such as sodium benzoate, citric acid monohydrate, potassium sorbate and combinations thereof. Preservatives, if present, may range from about 0.1 wt % to about 1.2 wt %, for instance, from about 0.2 wt % to about 0.6 wt %. For example, a combination of about 0.025 wt % to 0.1 wt % sodium benzoate, about 0.1 wt % to about 1 wt % citric acid monohydrate, and about 0.025 wt % to 0.1 wt % potassium sorbate may be used in the liquid formulation. In one embodiment, a combination of about 0.025 wt % to 0.050 wt % sodium benzoate, about 0.2 wt % to about 0.5 wt % citric acid monohydrate, and about 0.025 wt % to 0.050 wt % potassium sorbate may be used in the liquid formulation.

One or more flavoring ingredients may be added to the liquid electrolyte formulation. The flavoring ingredients may be present from about 0.1 wt % to about 0.8 wt %, or from about 0.2 wt % to about 0.5 wt %. The flavoring ingredients used are stain-free and are made with all natural flavorings. The flavoring agents may be non-polar (organic) oils which, by themselves, may not be easily suspended in water or liquid. The addition of acacia gum helps emulsify the agents and keep the flavoring ingredients suspended.

In one embodiment, the liquid electrolyte formulation is prepared into a popsicle form. The popsicle formulation is similar to the liquid electrolyte formulation, but further comprises one or more food additives that may be viscosity modifiers or thickeners to stabilize emulsions in the popsicle product. The food additives are typically present in amounts ranging from about 0.06 wt % to about 0.6 wt %, for instance, from about 0.12 wt % to about 0.3 wt %. Suitable food additives include polysaccharide food gums that can add viscosity to the mix and the unfrozen phase of the popsicle formulation. Addition of these food additives can assist in preventing the popsicle from becoming coarse, controlling the degree of the hardness and extending the shelf life by limiting ice recrystallization during storage. Exemplary food additives suitable for the popsicle liquid electrolyte formulation include, but not limited to, sodium carboxymethyl cellulose (CMC gum), Locust Bean Gum, Guar Gum, xanthan gum, sodium alginate, carrageenan, gelatin, and combinations thereof. For example, the popsicle electrolyte formulation may comprise sodium carboxymethylcellulose (CMC gum) ranging from about 0.06 wt % to about 0.6 wt %, from about 0.12 wt % to about 0.3 wt %, or from 0.15 wt % to about 0.25 wt %.

Exemplary ingredients and concentration range of the ingredients for regular liquid or beverage electrolyte formulations and popsicle liquid electrolyte formulations are shown as in Tables 1-4, below.

TABLE 1

A popsicle liquid electrolyte formula

| Ingredient | wt % (based on total weight of liquid) |
|---|---|
| Sodium Benzoate | 0.025% to 0.1% |
| Sodium Citrate | 0.1% to 1.0% |
| Citric Acid Monohydrate | 0.1% to 1.0% |
| CMC Gum (Sodium Carboxymethylcellulose) | 0.06% to 0.60% |
| Potassium Chloride | 0.05% to 0.25% |
| Potassium Sorbate | 0.025% to 0.10% |
| Dextrose | 0.6% to 15.0% |
| Fructose | 0.1% to 5.0% |
| Sucralose | 0.006% to 0.06% |
| Calcium Chloride | 0.08% to 0.5%. |
| Tri-Potassium Citrate Monohydrate | 0.02% to 0.10% |
| *Acacia* Gum | 0.05% to 10.0% |
| All Natural and Stain-free Flavors | 0.10% to 0.80% |
| Water | 65.4% to 98.7% |

TABLE 2

A liquid electrolyte formula

| Ingredient | wt % (based on total weight of liquid) |
|---|---|
| Sodium Benzoate | 0.025% to 0.1% |
| Sodium Citrate | 0.1% to 1.0% |
| Citric Acid Monohydrate | 0.1% to 1.0% |
| Sodium Chloride | 0.00% to 1.20% |
| Potassium Chloride | 0.05% to 0.25% |
| Potassium Sorbate | 0.025% to 0.10% |
| Dextrose | 0.6% to 15.0% |
| Fructose | 0.1% to 5.0% |
| Sucralose | 0.006% to 0.06% |
| Calcium Chloride | 0.08% to 0.5%. |
| Tri-Potassium Citrate Monohydrate | 0.02% to 0.10% |
| *Acacia* Gum | 0.05% to 10.0% |
| All Natural and Stain-free Flavors | 0.10% to 0.80% |
| Water | 64.8% to 98.8% |

TABLE 3

A popsicle liquid electrolyte formula

| Ingredient | wt % (based on total weight of liquid) |
|---|---|
| Sodium Benzoate | 0.025% to 0.050% |
| Sodium Citrate | 0.2% to 0.5% |
| Citric Acid Monohydrate | 0.2% to 0.5% |
| CMC Gum (Sodium Carboxymethylcellulose) | 0.12% to 0.30% |
| Potassium Chloride | 0.05% to 0.12% |
| Potassium Sorbate | 0.025% to 0.050% |
| Dextrose | 1.2% to 3.0% |
| Fructose | 0.3% to 0.7% |
| Sucralose | 0.006% to 0.03% |
| Calcium Chloride | 0.08% to 0.22% |
| Tri-Potassium Citrate Monohydrate | 0.02% to 0.10% |
| *Acacia* Gum | 0.05% to 2.00% |
| All Natural and Stain-free Flavors | 0.10% to 0.80% |
| Water | 91.6% to 97.7% |

TABLE 4

A liquid electrolyte formula

| Ingredient | wt % (based on total weight of liquid) |
|---|---|
| Sodium Benzoate | 0.025% to 0.050% |
| Sodium Citrate | 0.2% to 0.5% |
| Citric Acid Monohydrate | 0.2% to 0.5% |
| Sodium Chloride | 0.00% to 0.60% |
| Potassium Chloride | 0.05% to 0.12% |
| Potassium Sorbate | 0.025% to 0.050% |
| Dextrose | 1.2% to 3.0% |
| Fructose | 0.3% to 0.7% |
| Sucralose | 0.006% to 0.03% |
| Calcium Chloride | 0.08% to 0.22% |
| Tri-Potassium Citrate Monohydrate | 0.02% to 0.10% |
| *Acacia* Gum | 0.05% to 2.00% |
| All Natural and Stain-free Flavors | 0.10% to 0.80% |
| Water | 91.3% to 97.8% |

The present invention also relates to a concentrated form of electrolyte formulation, used to prepare the liquid or beverage electrolyte formulation already described herein. As used herein, the term "concentrate" or "concentrated form" may refer to a concentrate that is either in liquid or gel form or in essentially dry mixture form. The concentrate is formulated to provide a final and complete liquid or beverage electrolyte formulation as already described herein when reconstituted or diluted with water or other liquid. The essentially dry mixture is typically in the form of a powder, or in the form of a single-serving tablet or capsule, or any other convenient form.

Powder Electrolyte Composition

Upon reconstitution in water or other liquids, the reconstituted powder electrolyte composition includes sufficient amounts of *Acacia* gum to increase the absorption of water, and/or electrolyte, and/or carbohydrate by modulating intestinal activity. The *Acacia* gum may be present in the powder composition in an amount from about 0.5 wt % to about 75 wt %, for instance, from about 1 wt % to about 70 wt %, from about 10 wt % to about 35 wt %, or from about 10 wt % to about 20 wt %.

The powder electrolyte composition comprises sodium citrate ranging from about 2 wt % to about 18 wt %, for instance, from about 4.7 wt % to about 11 wt %, or from about 6.2 wt % to about 9.4 wt %.

The powder electrolyte composition comprises tri-potassium citrate monohydrate ranging from about 0.4 wt % to about 4 wt %, for instance, from about 0.8 wt % to about 1.9 wt %, or from about 1.0 wt % to about 1.6 wt %.

The powder electrolyte composition comprises sufficiently low amounts of sodium chloride. Typically, the sodium chloride content of the powder electrolyte composition may be about 3 wt % or less. For example, the sodium chloride content may range from about 0.3 wt % to about 3 wt %, or from about 0.6 wt % to about 1.4 wt %. In one embodiment, the sodium chloride content may be about 1.1 wt % or less.

The powder electrolyte composition also comprises sufficiently low amounts of potassium chloride. Typically, the potassium chloride content of the powder electrolyte composition may be about 6 wt % or less. For example, the potassium chloride content may range from about 0.6 wt % to about 6 wt %, or from about 1.2 wt % to about 2.8 wt %. In one embodiment, the potassium chloride content may be about 2.1 wt % or less.

The powder electrolyte composition may comprise calcium chloride ranging from about 0.6 wt % to about 6 wt %, for instance, from about 1.2 wt % to about 2.9 wt %, or from about 1.6 wt % to about 2.5 wt %.

The powder electrolyte composition may comprise carbohydrate (e.g., sugars) ranging from about 30 wt % to about 87 wt %, for instance, from about 35 wt % to about 83 wt %. Suitable carbohydrates include, but are not limited to, dextrose, fructose, sucrose, maltose, maltodextrin, galactose, trehalose, fructo-oligosaccharides, beta-glucan, trioses, and combinations thereof. For example, a combination of about 28 wt % to about 66.1 wt % dextrose and about 2 wt % to about 20 wt % fructose may be present in the powder composition. In one embodiment, a combination of about 283 wt % to about 66.1 wt % dextrose and about 7.0 wt % to about 16.3 wt % fructose may be present in the powder composition. In another embodiment, a combination of about 39 wt % to about 58 wt % dextrose and about 9 wt % to about 14 wt % fructose may be present in the powder composition.

One or more sugar substitutes may be used in the powder electrolyte composition. Suitable sugar substitutes used in the powder composition include, for example, sucralose, saccharin, aspartame, acesulfame potassium, stevia, neotame and combinations thereof. Sugar substitutes, if present, may range from about 0.15 wt % to about 1 wt %, for instance, from about 0.15 wt % to about 0.35 wt %. For example, sucralose may be used in the powder composition in a range from about 0.15 wt % to about 1 wt %, or from about 0.15 wt % to about 0.35 wt %. In one embodiment, about 0.2 wt % to about 0.3 wt % sucralose may be used in the powder composition.

The powder electrolyte composition may further comprise preservatives, such as sodium benzoate, citric acid monohydrate, potassium sorbate and combinations thereof. Preservatives, if present, may range from about 2.8 wt % to about 23 wt %, for instance, from about 6 wt % to about 13.7 wt %. For example, a combination of about 0.025 wt % to 2 wt % sodium benzoate, about 2.5 wt % to about 18 wt % citric acid monohydrate and about 0.3 wt % to about 3 wt % potassium sorbate may be used in the powder composition. In one embodiment, a combination of about 0.6 wt % to 1.1 wt % sodium benzoate, about 4.9 wt % to about 11.5 wt % citric acid monohydrate and about 0.6 wt % to about 1.1 wt % potassium sorbate may be used in the powder composition. In another embodiment, a combination of about 0.85 wt % to 1.1 wt % sodium benzoate, about 6.5 wt % to about 9.8 wt % citric acid monohydrate and about 0.85 wt % to about 1.1 wt % potassium sorbate may be used in the powder composition.

One or more flavoring ingredients may be added to the powder electrolyte composition. The flavoring ingredients may be dry flavors and may be stain-free and made with all natural flavorings. The dry flavors may be present from about 1 wt % to about 14 wt %, for instance, from about 1.3 wt % to about 7.9 wt %.

Tablet Electrolyte Composition

Upon reconstitution in water or other liquids, the reconstituted tablet electrolyte composition includes sufficient amounts of *Acacia* gum to increase the absorption of water, and/or electrolyte, and/or carbohydrate by modulating intestinal activity. The Acacia gum may be present in the powder composition in an amount from about 0.5 wt % to about 75 wt %, for instance, from about 1 wt % to about 70 wt %, from about 10 wt % to about 35 wt %, or from about 10 wt % to about 20 wt %.

The tablet electrolyte composition comprises sodium citrate ranging from about 2 wt % to about 18 wt %, for instance, from about 4.7 wt % to about 11 wt %, or from about 6.2 wt % to about 9.4 wt %.

The tablet electrolyte composition comprises tri-potassium citrate monohydrate ranging from about 0.4 wt % to about 4 wt %, for instance, from about 0.8 wt % to about 1.9 wt %, or from about 1.0 wt % to about 1.6 wt %.

The tablet electrolyte composition comprises sufficiently low amounts of sodium chloride. Typically, the sodium chloride content of the tablet electrolyte composition may be about 3 wt % or less. For example, the sodium chloride content may range from about 0.3 wt % to about 3 wt %, or from about 0.6 wt % to about 1.4 wt %. In one embodiment, the sodium chloride content may be about 1.1 wt % or less.

The tablet electrolyte composition also comprises sufficiently low amounts of potassium chloride. Typically, the potassium chloride content of the tablet electrolyte composition may be about 6 wt % or less. For example, the potassium chloride content may range from about 0.6 wt % to about 6 wt %, or from about 1.2 wt % to about 2.8 wt %. In one embodiment, the potassium chloride content may be about 2.1 wt % or less.

The tablet electrolyte composition may comprise calcium chloride ranging from about 0.6 wt % to about 6 wt %, for instance, from about 1.2 wt % to about 2.9 wt % In one embodiment, about 0.1 wt % to about 8 wt % tri-calcium citrate is used to replace calcium chloride for providing calcium ion source. In one embodiment, tricalcium citrate ranges from about 0.2 wt % to about 3.9 wt %. In another embodiment, tricalcium citrate ranges from about 1.1 wt % to about 3.0 wt %. Calcium citrate may be used to decrease the hydroscopicity and discoloring of tablet composition over time and to increase the storage time or shelf life of the tablet electrolyte composition.

The tablet electrolyte composition may comprise carbohydrate (e.g., sugars) ranging from about 30 wt % to about 87 wt %, for instance, from about 35 wt % to about 83 wt %. Suitable carbohydrates include, but are not limited to, dextrose, fructose, sucrose, maltose, maltodextrin, galactose, trehalose, fructo-oligosaccharides, beta-glucan, trioses, and combinations thereof. For example, a combination of about 28 wt % to about 66.1 wt % dextrose and about 2 wt % to about 20 wt % fructose may be present in the powder composition. In one embodiment, a combination of about 28.3 wt % to about 66.1 wt % dextrose and about 7.0 wt % to about 16.3 wt % fructose may be present in the tablet composition.

In another embodiment, a combination of about 39 wt % to about 58 wt % dextrose and about 9 wt % to about 14 wt % fructose may be present in the tablet composition.

One or more sugar substitutes may be used in the tablet electrolyte composition. Suitable sugar substitutes used in the tablet composition include, for example, sucralose, saccharin, aspartame, acesulfame potassium, stevia, neotame and combinations thereof. Sugar substitutes, if present, may range from about 0.15 wt % to about 1 wt %, for instance, from about 0.15 wt % to about 0.35 wt %. For example, sucralose may be used in the powder composition in a range from about 0.15 wt % to about 1 wt %, or from about 0.15 wt % to about 0.35 wt %. In one embodiment, about 0.2 wt % to about 0.3 wt % sucralose may be used in the tablet composition.

The tablet electrolyte composition may further comprise preservatives, such as sodium benzoate, citric acid monohydrate, potassium sorbate and combinations thereof. Preservatives, if present, may range from about 2.8 wt % to about 23 wt %, for instance, from about 6 wt % to about 13.7 wt %. For example, a combination of about 0.025 wt % to 2 wt % sodium benzoate, about 2.5 wt % to about 18 wt % citric acid monohydrate and about 0.3 wt % to about 3 wt % potassium sorbate may be used in the tablet composition. In one embodiment, a combination of about 0.6 wt % to 1.1 wt % sodium benzoate, about 4.9 wt % to about 11.5 wt % citric acid monohydrate and about 0.6 wt % to about 1.1 wt % potassium sorbate may be used in the tablet composition. In another embodiment, a combination of about 0.85 wt % to 1.1 wt % sodium benzoate, about 6.5 wt % to about 9.8 wt % citric acid monohydrate and about 0.85 wt % to about 1.1 wt % potassium sorbate may be used in the tablet composition.

One or more flavoring ingredients may be added to the tablet electrolyte composition. The flavoring ingredients may be dry flavors and may be stain-free and made with all natural flavorings. The dry flavors may be present from about 1 wt % to about 14 wt %, for instance, from about 1.3 wt % to about 7.9 wt %.

The tablet electrolyte composition may further comprise one or more lubricant agents. Small amounts of lubricants are typically added to help the pressing process of the tablets, for example to help enhance product flow, ensure easy ejection from the dies, and to prevent product sticking to machine parts. Lubricants, if present, may range from about 0.1 wt % to about 10 wt %, for instance, from about 0.1 wt % to about 5 wt %. Suitable lubricants include, but not limited to polyethylene glycol (PEG, such as MW 4000-6000), sucrose ester, magnesium stearate, calcium stearate, stearic acid (stearin), hydrogenated oil (sterotex, lubritab, cutina), and sodium stearyl fumarate, sodium lauryl sulfate (SLS), sodium benzoate, glyceryl palmitostearate (Precirol), glyceryl behenate (Compitrol 888), and combinations thereof. For example, the tablet electrolyte composition may comprise sucrose ester as a lubricant, ranging from about 0.1 wt % to about 10 wt %, from about 0.1 wt % to about 5 wt %, or from about 0.1 wt % to about 2 wt %. Other means of forming tablets without the use of lubricants can also be used.

The powder and tablet electrolyte compositions may be prepared to be completely soluble to water. A beverage can be prepared by diluting the concentrated liquid electrolyte formulation or by reconstitution of powder or tablet electrolyte composition in water or any other appropriate liquids. Such reconstitution is made with the requisite amounts of water/liquid to ensure that the beverage to be consumed contains the active and effective amounts of ingredients in the proportions. One skilled in the art will be able to determine the amount of water/liquid required to prepare the beverage based on the knowledge of this invention.

In addition, the tablet electrolyte composition may also be prepared as a chewable tablet or capsule. The effective ingredients of the tablet composition may be released upon mixing with a bodily fluid, such as saliva.

Exemplary ingredients and a percentage range of the ingredients for powder electrolyte compositions and tablet electrolyte compositions are shown in Tables 5-8, below.

TABLE 5

A powder electrolyte formula

| Ingredient | wt % (based on total weight of powder) |
| --- | --- |
| Sodium Benzoate | 0.025% to 2.0% |
| Sodium Citrate | 2.0% to 18.0% |
| Citric Acid Monohydrate | 2.5% to 18.0% |
| Sodium Chloride | 0.3% to 3.0% |
| Potassium Chloride | 0.6% to 6.0% |
| Potassium Sorbate | 0.3% to 3.0% |
| Dextrose | 28.3% to 66.1% |
| Fructose | 2.0% to 20.0% |
| Sucralose | 0.15% to 1.0% |
| Calcium Chloride | 0.6% to 6.0% |
| Tri-Potassium Citrate Monohydrate | 0.4% to 4.0% |
| *Acacia* Gum | 0.5% to 75.0% |
| Dry Flavors | 1.0% to 14.0% |

TABLE 6

A tablet electrolyte formula

| Ingredient | wt % (based on total weight of tablet) |
| --- | --- |
| Sodium Benzoate | 0.025% to 2.0% |
| Sodium Citrate | 2.0% to 18.0% |
| Citric Acid Monohydrate | 2.5% to 18.0% |
| Sodium Chloride | 0.3% to 3.0% |
| Potassium Chloride | 0.6% to 6.0% |
| Potassium Sorbate | 0.3% to 3.0% |
| Dextrose | 28.3% to 66.1% |
| Fructose | 2.0% to 20.0% |
| Sucralose | 0.15% to 1.0% |
| Tri-calcium Citrate | 0.1% to 8.0% |
| Tri-Potassium Citrate Monohydrate | 0.4% to 4.0% |
| *Acacia* Gum | 0.5% to 75.0% |
| Sucrose Ester | 0.1% to 10.0% |
| Dry Flavors | 1.0% to 14.0% |

TABLE 7

A powder electrolyte formula

| Ingredient | wt % (based on total weight of powder) |
| --- | --- |
| Sodium Benzoate | 0.6% to 1.1% |
| Sodium Citrate | 4.7% to 11.0% |
| Citric Acid Monohydrate | 4.9% to 11.5% |
| Sodium Chloride | 0.6% to 1.4% |
| Potassium Chloride | 1.2% to 2.8% |
| Potassium Sorbate | 0.6% to 1.1% |
| Dextrose | 28.3% to 66.1% |
| Fructose | 7.0% to 16.3% |
| Sucralose | 0.15% to 0.35% |
| Calcium Chloride | 1.2% to 2.9% |
| Tri-Potassium Citrate Monohydrate | 0.8% to 1.9% |
| *Acacia* Gum | 1.0% to 35.0% |
| Dry Flavors | 1.0% to 14.0% |

TABLE 8

A tablet electrolyte formula

| Ingredient | wt % (based on total weight of tablet) |
|---|---|
| Sodium Benzoate | 0.6% to 1.1% |
| Sodium Citrate | 4.7% to 11.0% |
| Citric Acid Monohydrate | 4.9% to 11.5% |
| Sodium Chloride | 0.6% to 1.4% |
| Potassium Chloride | 1.2% to 2.8% |
| Potassium Sorbate | 0.6% to 1.1% |
| Dextrose | 28.3% to 66.1% |
| Fructose | 7.0% to 16.3% |
| Sucralose | 0.15% to 0.35% |
| Tri-calcium Citrate | 0.2% to 3.9% |
| Tri-Potassium Citrate Monohydrate | 0.8% to 1.9% |
| *Acacia* Gum | 1.0% to 35.0% |
| Sucrose Ester | 0.1% to 5.0% |
| Dry Flavors | 1.0% to 14.0% |

Dietary Fiber Source

In another aspect of the invention, the *Acacia* gum in the electrolyte formulation can be replaced by a dietary fiber. Any dietary fiber known to one skilled in the art may be used. Alternatively, a dietary fiber source may be added to the electrolyte formulation in addition to the *Acacia* gum. The dietary fiber used in the electrolyte formulation may include a mixture of dietary fibers.

Dietary fiber is the indigestible portion of plants. As used herein, the term "dietary fiber" refers to one or more dietary components derived from plant material, or analogous carbohydrates, that are generally resistant to digestion and absorption in the human small intestine. Dietary components derived from plant material include, but are not limited to, various polysaccharides, oligosaccharides, polyfructans, and lignins that are resistant to digestion. The term "analagous carbohydrates" in the above definition refers to carbohydrate compounds that may not be specifically derived from plant material, but that are otherwise resistant to digestion and absorption in the human small intestine (e.g., a synthetic non-digestible polysaccharide or oligosaccharide, such as polydextrose).

Medical and nutritional studies show that dietary fiber can provide numerous benefits to human health. For example, soluble fiber can be fermented by colonic bacteria providing energy to the body; and the fermentation of the fiber can also stimulate mucosal blood flow and cell proliferation and promote adaptive responses to small intestinal resection and colonic anastomosis, thereby enhancing water and electrolyte absorption. See Scheppach, "Effects of short chain fatty acids on gut morphology and function," Gut 35 S35-S38 (1994).

Dietary fiber sources suitable for use in the electrolyte formulation include both water-soluble fiber and water-insoluble fiber.

In one embodiment, the dietary fiber is a soluble fiber including but not limited to legumes (e.g., peas, lentils, and beans such as soybeans), oat bran, rye, chia, seeds, barley, fruits and fruit juices (e.g., prune juice, plum, berriers, bananas, and the insides of apples and pears), vegetables (e.g., broccoli, carrots and Jerusalem artichokes), root tubers and root vegetables (e.g., sweet potatoes and onions), psyllium seed, gum, vegetable fiber gum and combinations thereof. Suitable soluble fibers include water-soluble plant pectins and pectic materials, galactomannans, arabanogalactans and water-soluble hemicellulose can act as soluble fiber; many plant "mucilages," gums, and soluble polysaccharides found in grains, seeds, or stems such as psyllium, guar, oat (beta glucans), astragalus (gum traganth), gum ghatti, and gum karaya (Sterculia gum); algal polysaccharides such as agar or carrageenan; other indigestible carbohydrates, such as maltodextrins or dextrins, produced by chemical or enzymatic digestion (e.g., partial hydrolysis) of starch, gums and other carbohydrate polymers; soluble cellulosic ethers and other derivatives such as carboxymethy cellulose; indigestible carbohydrate polymers artificially prepared using bacterial enzymes; and non-digestible storage carbohydrates such as inulin.

Suitable insoluble fibers include whole grains, rice, wheat and corn bran, cereals and pasta, nuts and seeds, potato skins, fruit skins (e.g., tomatoes), cellulose, hemicelluloses, flax seeds, lignans, certain fruits (e.g., avocado and bananas), vegetables (e.g., green beans, cauliflower, zucchini, courgette, celery, and nopal), and psyllium husk. Many fruits and vegetables contain both soluble and insoluble fiber.

The dietary fiber in the electrolyte formulation may also include a mixture of sources of dietary fiber, depending upon the factors such as desired taste, desired texture, and so on.

In one embodiment, the dietary fiber is selected from the group consisting of legumes (such as beans, lentils and peas), bran, prunes, asian pear, quinoa, rubus fruits (e.g., raspberry and blackberry), includespsyllium, seed husk, beta-glucan from oat gran, whole oats, oatrim, rolled oats, whole grain or dry-milled barley, inulins (such as those extracted from enriched plant sources, for instance, chicory roots and Jerusalem artichokes), resistant destrin, fructans, cellulose, frutooligosaccharides, oligo- or polysacchrides, xanthan gum, vegetable gums such as guar gum and *acacia* gum, and combinations thereof.

Methods to Prevent Dehydration

Some embodiments of the invention relate to methods of treating or preventing dehydration, or diseases or disorders related to dehydration. The method comprises the step of administering to a subject in need thereof the electrolyte formulation described in this invention. The ingredients, forms, and percentage of the ingredients of the suitable electrolyte formulation, including all examples and preferred embodiments, have been described herein. One example of administering the electrolyte formulation of the invention is through oral administration. For example, the liquid/beverage electrolyte formulation of the invention can be prepared as a drinkable liquid/beverage; the concentrated liquid electrolyte formulation can be diluted with water or liquids or other beverage; the powder or tablet electrolyte composition of the invention can be reconstituted in water or liquids or other beverages; or the tablet electrolyte composition can be prepared as a chewable tablet. The amount of electrolyte formulation administered may be from about 0.05 to about 5 Liters. The effective amount of electrolyte formulation may vary depending on the body mass of the subject and the degree of dehydration.

The electrolyte formulation of the invention, after administered to a subject, is designed to replenish the body's water, electrolyte and/or carbohydrate levels. It can be used for treating or preventing dehydration (hypohydration), hyponatremia and/or hypovolemia caused by exercise, changes in environment such as change in altitude, diaphoresis, diarrhea, vomiting, intoxication, starvation, and combinations thereof.

The electrolyte formulation of the invention assists in the increased absorption of water, electrolytes and carbohydrate by modulating an intestinal activity. Therefore, one benefit of the electrolyte formulation of the invention is the efficacy on patients suffering from intestinal disorders or diseases. For example, the electrolyte formulation of the invention can be used to treat or prevent dehydration of subjects who are suffering from an intestinal inflammation such as gastroenteritis, ileitis, colitis, appendicitis, inflammatory bowel disease, diarrhea, Crohn's disease, enteritis and combinations thereof.

In addition, because the electrolyte formulation of the invention increases absorption of water and electrolytes, it allows for a low volume intake in a subject while still effectively rehydrating the subject with sufficient water and maintaining healthy blood-electrolyte levels in the subject.

Methods to Reduce or Prevent Taste Fatigue

Some embodiments of the invention relate to methods of reducing or preventing taste fatigue of a subject consuming an electrolyte formulation. The method comprises the step of administering to a subject in need thereof the electrolyte formulation described in this invention. The ingredients, forms, and percentage of the ingredients of the suitable electrolyte formulation, including all examples and preferred embodiments have been described herein. In one embodiment of the invention, the electrolyte formulation has been formulated to address taste sensitivity. The ingredient of the electrolyte formulation is prepared in such a proportion that the formulation contains sufficiently low amounts of sodium chloride and potassium chloride to reduce the saline and/or bitter taste while maintaining an effective amount of chloride, sodium, potassium, and calcium ions in the electrolyte formulation, thereby reducing or preventing taste fatigue of the subject consuming the electrolyte formulation. For example, addition of tripotasium citrate monohydrate in the electrolyte formulation to eliminate or reduce sodium chloride and potassium chloride from the formulation has significantly reduced the "salty" taste and prevented a bitter taste.

One benefit of the electrolyte formulation of the invention is the ability to efficiently administer the formulation to an older population, such as geriatric subject, many of which suffer from dehydration. Administration of a lower-volume hydration formulation is generally desirable for the geriatric subject. In this case, the electrolyte formulation of the invention allows for a low volume intake in a subject while still effectively rehydrating the subject with sufficient water and maintaining healthy blood-electrolyte levels in the subject. In addition, because of the reduced taste fatigue by administering the electrolyte formulation of the invention, the formulation possesses superior sensory qualities, stimulates increased voluntary consumption, and supports the physiological response to continue drinking. This positive hydration and rehydration cycle helps effectively treat or prevent of dehydration for geriatric patients.

EXAMPLES

Example 1

Popsicle Electrolyte Formulation

TABLE 9

Ingredients for preparing a 208 gallon popsicle electrolyte formulation.

| Ingredient | weight |
| --- | --- |
| Sodium Benzoate | 0.80 lbs. |
| Sodium Citrate | 5.837 lbs. |
| Citric Acid Monohydrate | 6.120 lbs. |
| CMC Gum (Sodium Carboxymethylcellulose) | 3.750 lbs. |
| Potassium Chloride | 1.501 lbs. |
| Potassium Sorbate | 0.80 lbs. |
| Dextrose | 25.00 lbs. |
| Fructose at 43.5% | 20.00 lbs. |
| Sucralose at 25.0% | 0.75 lbs. |
| Calcium Chloride | 2.251 lbs. |

TABLE 9-continued

Ingredients for preparing a 208 gallon popsicle electrolyte formulation.

| Ingredient | weight |
| --- | --- |
| Tri-Potassium Citrate Monohydrate | 1.00 lbs. |
| Acacia Gum | 8.676 lbs. |
| All Flavors (All Natural and Stain-free) added at end of process | 0.30% |

Example 2

Tablet Electrolyte Formulation

TABLE 10

Ingredients for preparing a 1000 unit mix
(e.g., to be reconstituted in 1000 liters water or liquids) tablet formula

| Ingredient | weight | wt % in the tablet |
| --- | --- | --- |
| Sodium Benzoate | 1.016 lbs | 1.07 |
| Sodium Citrate | 7.436 lbs | 7.81 |
| Citric Acid Monohydrate | 7.763 lbs. | 8.15 |
| Sodium Chloride | 0.953 lbs | 1.00 |
| Potassium Chloride | 1.907 lbs. | 2.00 |
| Potassium Sorbate | 1.016 lbs. | 1.07 |
| Dextrose | 44.78 lbs. | 47.0 |
| Fructose | 11.02 lbs. | 11.6 |
| Sucralose | 0.238 lbs. | 0.25 |
| Calcium Chloride | 1.957 lbs. | 2.06 |
| Tri-Potassium Citrate Monohydrate | 1.270 lbs. | 1.33 |
| Dry Flavoring | 4.409 lbs. | 4.63 |
| Lubrication Agent | 0.419 lbs. | 0.44 |
| Acacia Gum | 11.02 lbs. | 11.6 |

The invention claimed is:

1. A liquid electrolyte formulation, comprising:
   about 0.05 wt % to about 10 wt % *Acacia* Gum (Gum Arabic),
   about 0.08 wt % to about 0.5 wt % calcium chloride,
   about 0.1 wt % to about 1.0 wt % sodium citrate,
   about 0.02 wt % to about 0.1 wt % tri-potassium citrate monohydrate,
   less than about 0.25 wt % potassium chloride,
   less than about 1.2 wt % sodium chloride, and
   water;
   wherein the *Acacia* Gum is present in sufficient amounts to increase the absorption of water by modulating intestinal activity;
   wherein the electrolyte formulation contains sufficiently low amounts of sodium chloride and potassium chloride to reduce the saline and/or bitter taste while maintaining an effective amount of chloride, sodium, potassium, and calcium ions in the electrolyte formulation; and
   wherein the electrolyte formulation has a pH ranging from about 3.9 to about 4.2.

2. The liquid electrolyte formation of claim 1, wherein the formulation increases the absorption of the sodium, potassium, and calcium ions.

3. The liquid electrolyte formation of claim 1, wherein the formulation increases the absorption of the carbohydrates.

4. A popsicle electrolyte formulation comprising the liquid electrolyte formulation of claim 3, and about 0.06 wt % to about 0.6 wt % polysaccharide gums selected from the group consisting of sodium carboxymethyl cellulose (CMC gum), Locust Bean Gum, Guar Gum, xanthan gum, sodium alginate, carrageenan, gelatin, and combinations thereof.

5. The liquid electrolyte formulation of claim 1, wherein the electrolyte formulation does not contain any sodium chloride.

6. The liquid electrolyte formulation of claim 1, further comprising about 0.7 wt % to about 20 wt % carbohydrate selected from the group consisting of dextrose, fructose, sucrose, maltose, maltodextrin, galactose, trehalose, fructo-oligosaccharides, beta-glucan, trioses, and combinations thereof.

7. The liquid electrolyte formulation of claim 1, further comprising about 0.006 wt % to about 0.06 wt % sugar substitutes selected from the group consisting of sucralose, saccharin, aspartame, acesulfame potassium, stevia, neotame and combinations thereof.

8. The liquid electrolyte formulation of claim 1, further comprising about 0.1 wt % to about 1.2 wt % preservatives selected from the group consisting of sodium benzoate, citric acid monohydrate, potassium sorbate and combinations thereof.

9. The liquid electrolyte formulation of claim 1, further comprising about 0.1 wt % to about 0.8 wt % of one or more natural and stain-free flavoring ingredients.

10. The liquid electrolyte formulation of claim 1, further comprising a dietary fiber.

11. The liquid electrolyte formulation of claim 10, wherein the dietary fiber is selected from the group consisting of legumes, oat bran, rye, chia, barley, fruits and fruit juices, vegetables, root tubers and root vegetables, psyllium seed, whole grains, rice, wheat and corn bran, cereals and pasta, nuts and seeds, potato skins, fruit skins, cellulose, hemicelluloses, flax seeds, lignans, psyllium husk, gum, vegetable fiber gum, and combinations thereof.

12. A powder electrolyte composition for reconstitution in water, comprising:
about 0.5 wt % to about 75 wt % *Acacia* Gum (Gum Arabic),
about 0.6 wt % to about 6 wt % calcium chloride,
about 2 wt % to about 18 wt % sodium citrate,
about 0.4 wt % to about 4 wt % tri-potassium citrate monohydrate,
less than about 6 wt % potassium chloride, and
less than about 3 wt % sodium chloride;
wherein, upon reconstitution in water, the *Acacia* Gum is present in sufficient amounts to increase the absorption of water by modulating intestinal activity;
wherein, upon reconstitution in water, the electrolyte formulation contains sufficiently low amounts of sodium chloride and potassium chloride to reduce the saline and/or bitter taste while maintaining an effective amount of chloride, sodium, potassium, and calcium ions in the electrolyte composition; and
wherein, upon reconstitution in water, the electrolyte composition has a pH ranging from about 3.9 to about 4.2.

13. The powder electrolyte composition of claim 12, wherein the composition increases the absorption of the sodium, potassium, and calcium ions.

14. The powder electrolyte composition of claim 12, further comprising about 30 wt % to about 87 wt % carbohydrate selected from the group consisting of dextrose, fructose, sucrose, maltose, maltodextrin, galactose, trehalose, fructo-oligosaccharides, beta-glucan, trioses, and combinations thereof.

15. The powder electrolyte composition of claim 12, further comprising about 0.15 wt % to about 1 wt % sugar substitutes selected from the group consisting of sucralose, saccharin, aspartame, acesulfame potassium, stevia, neotame and combinations thereof.

16. The powder electrolyte composition of claim 12, further comprising about 2.8 wt % to about 23 wt % preservatives selected from the group consisting of sodium benzoate, citric acid monohydrate, potassium sorbate and combinations thereof.

17. The powder electrolyte composition of claim 12, further comprising about 1 wt % to about 14 wt % of one or more dry flavoring ingredients.

18. The powder electrolyte composition of claim 12, further comprising a dietary fiber.

19. The powder electrolyte composition of claim 18, wherein the dietary fiber is selected from the group consisting of legumes, oat bran, rye, chia, barley, fruits and fruit juices, vegetables, root tubers and root vegetables, psyllium seed, whole grains, rice, wheat and corn bran, cereals and pasta, nuts and seeds, potato skins, fruit skins, cellulose, hemicelluloses, flax seeds, lignans, psyllium husk, gum, vegetable fiber gum, and combinations thereof.

20. A tablet electrolyte composition for reconstitution in water, comprising:
about 0.5 wt % to about 75 wt % *Acacia* Gum (Gum Arabic),
about 0.1 to about 8 wt % tri-calcium citrate,
about 2 wt % to about 18 wt % sodium citrate,
about 0.4 wt % to about 4 wt % tri-potassium citrate monohydrate,
less than about 6 wt % potassium chloride, and
less than about 3 wt % sodium chloride;
wherein, upon reconstitution in water, the *Acacia* Gum is present in sufficient amounts to increase the absorption of water by modulating intestinal activity;
wherein, upon reconstitution in water, the electrolyte composition contains sufficiently low amounts of sodium chloride and potassium chloride to reduce the saline and/or bitter taste while maintaining an effective amount of chloride, sodium, potassium, and calcium ions in the electrolyte composition; and
wherein, upon reconstitution in water, the electrolyte composition has a pH ranging from about 3.9 to about 4.2.

21. The tablet electrolyte composition of claim 20, wherein the composition increases the absorption of the sodium, potassium, and calcium ions.

22. The tablet electrolyte composition of claim 20, further comprising about 30 wt % to about 87 wt % carbohydrate selected from the group consisting of dextrose, fructose, sucrose, maltose, maltodextrin, galactose, trehalose, fructo-oligosaccharides, beta-glucan, trioses, and combinations thereof.

23. The tablet electrolyte composition of claim 20, further comprising about 0.15 wt % to about 1 wt % sugar substitutes selected from the group consisting of sucralose, saccharin, aspartame, acesulfame potassium, stevia, neotame and combinations thereof.

24. The tablet electrolyte composition of claim 20, further comprising about 2.8 wt % to about 23 wt % preservatives selected from the group consisting of sodium benzoate, citric acid monohydrate, potassium sorbate and combinations thereof.

25. The tablet electrolyte composition of claim 20, further comprising about 0.1 wt % to about 10 wt % sucrose ester.

26. The tablet electrolyte composition of claim 20, further comprising about 1 wt % to about 14 wt % of one or more dry flavoring ingredient.

27. The tablet electrolyte composition of claim 20, wherein the tablet is chewable.

28. A beverage prepared by reconstituting in water the tablet electrolyte composition of claim 20.

29. The tablet electrolyte composition of claim 20, further comprising a dietary fiber.

30. The tablet electrolyte composition of claim 29, wherein the dietary fiber is selected from the group consisting of legumes, oat bran, rye, chia, barley, fruits and fruit juices, vegetables, root tubers and root vegetables, psyllium seed, whole grains, rice, wheat and corn bran, cereals and pasta, nuts and seeds, potato skins, fruit skins, cellulose, hemicelluloses, flax seeds, lignans, psyllium husk, gum, vegetable fiber gum, and combinations thereof.

31. A method of reducing or preventing taste fatigue of a subject consuming a liquid electrolyte formulation, comprising the step of:
administering to a subject a liquid electrolyte formulation comprising:
about 0.05 wt % to about 10 wt % *Acacia* Gum (Gum Arabic),
about 0.08 wt % to about 0.5 wt % calcium chloride,
about 0.1 wt % to about 1.0 wt % sodium citrate,
about 0.02 wt % to about 0.1 wt % tri-potassium citrate monohydrate,
less than about 0.25 wt % potassium chloride,
less than about 1.2 wt % sodium chloride, and
water
wherein the formulation contains sufficiently low amounts of sodium chloride and potassium chloride to reduce the saline and/or bitter taste while maintaining an effective amount of chloride, sodium, potassium, and calcium ions in the electrolyte formulation, thereby reducing or preventing taste fatigue of the subject consuming the electrolyte formulation.

32. The method of claim 31, wherein the electrolyte formulation does not contain any sodium chloride.

33. The method of claim 31, wherein the subject is a geriatric subject.

34. The method of claim 31, wherein the electrolyte formulation further comprises a dietary fiber.

35. The method of claim 34, wherein the dietary fiber is selected from the group consisting of legumes, oat bran, rye, chia, barley, fruits and fruit juices, vegetables, root tubers and root vegetables, psyllium seed, whole grains, rice, wheat and corn bran, cereals and pasta, nuts and seeds, potato skins, fruit skins, cellulose, hemicelluloses, flax seeds, lignans, psyllium husk, gum, vegetable fiber gum, and combinations thereof.

36. The method of reducing or preventing taste fatigue of a subject, wherein the electrolyte formulation is a powder electrolyte composition that has been reconstituted in water, the powder composition comprising:
about 0.5 wt % to about 75 wt % *Acacia* Gum (Gum Arabic),
about 0.6 wt % to about 6 wt % calcium chloride,
about 2 wt % to about 18 wt % sodium citrate,
about 0.4 wt % to about 4 wt % tri-potassium citrate monohydrate,
less than about 6 wt % potassium chloride, and
less than about 3 wt % sodium chloride.

37. The method of claim 36, where the subject is a geriatric subject.

38. The method of reducing or preventing taste fatigue of a subject, wherein the electrolyte formulation is a tablet electrolyte composition that has been reconstituted in water, the tablet composition comprising:
about 0.5 wt % to about 75 wt % *Acacia* Gum (Gum Arabic),
about 0.1 to about 8 wt % tri-calcium citrate,
about 2 wt % to about 18 wt % sodium citrate,
about 0.4 wt % to about 4 wt % tri-potassium citrate monohydrate,
less than about 6 wt % potassium chloride, and
less than about 3 wt % sodium chloride.

39. The method of claim 38, where the subject is a geriatric subject.

40. A method for treating or preventing dehydration, comprising the step of:
administering to a subject in need thereof an electrolyte formulation comprising:
about 0.5 wt % to about 75 wt % *Acacia* Gum (Gum Arabic),
about 0.6 wt % to about 6 wt % calcium chloride,
about 2 wt % to about 18 wt % sodium citrate,
about 0.4 wt % to about 4 wt % tri-potassium citrate monohydrate,
less than about 6 wt % potassium chloride, and
less than about 3 wt % sodium chloride
wherein the *Acacia* Gum is present in sufficient amounts to increase the absorption of water by modulating intestinal activity, thereby treating or preventing dehydration of the subject.

41. The method of claim 40, wherein the subject is a geriatric subject suffering from dehydration.

42. The method of claim 40, wherein the subject is suffering from an intestinal disease.

43. The method of claim 42, wherein the intestinal disease is an intestinal inflammation selected from the group consisting of gastroenteritis, ileitis, colitis, appendicitis, inflammatory bowel disease, diarrhea, Crohn's disease, enteritis and combinations thereof.

44. The method of claim 40, wherein the electrolyte formulation further comprises a dietary fiber.

45. The method of claim 44, wherein the dietary fiber is selected from the group consisting of legumes, oat bran, rye, chia, barley, fruits and fruit juices, vegetables, root tubers and root vegetables, psyllium seed, whole grains, rice, wheat and corn bran, cereals and pasta, nuts and seeds, potato skins, fruit skins, cellulose, hemicelluloses, flax seeds, lignans, psyllium husk, gum, vegetable fiber gum, and combinations thereof.

46. The method for treating or preventing dehydration, wherein the electrolyte formulation is a powder electrolyte composition that has been reconstituted in water, the powder composition comprising:
about 0.5 wt % to about 75 wt % *Acacia* Gum (Gum Arabic),
about 0.6 wt % to about 6 wt % calcium chloride,
about 2 wt % to about 18 wt % sodium citrate,
about 0.4 wt % to about 4 wt % tri-potassium citrate monohydrate,
less than about 6 wt % potassium chloride, and
less than about 3 wt % sodium chloride.

47. The method of claim 46, where the subject is a geriatric subject suffering from dehydration.

48. The method of claim 46, wherein the subject is suffering from an intestinal disease.

49. The method for treating or preventing dehydration, wherein the electrolyte formulation is a tablet electrolyte composition that has been reconstituted in water, the tablet composition comprising:
about 0.5 wt % to about 75 wt % *Acacia* Gum (Gum Arabic),
about 0.1 to about 8 wt % tri-calcium citrate,
about 2 wt % to about 18 wt % sodium citrate,
about 0.4 wt % to about 4 wt % tri-potassium citrate monohydrate,
less than about 6 wt % potassium chloride, and
less than about 3 wt % sodium chloride.

50. The method of claim 49, where the subject is a geriatric subject suffering from dehydration.

51. The method of claim 49, wherein the subject is suffering from an intestinal disease.

52. A liquid electrolyte formulation, comprising:
about 0.05 wt % to about 10 wt % of a dietary fiber,
about 0.08 wt % to about 0.5 wt % calcium chloride,
about 0.1 wt % to about 1.0 wt % sodium citrate,
about 0.02 wt % to about 0.1 wt % tri-potassium citrate monohydrate,
less than about 0.25 wt % potassium chloride,
less than about 1.2 wt % sodium chloride, and
water;
wherein the dietary fiber is present in sufficient amounts to increase the absorption of water by modulating intestinal activity;
wherein the electrolyte formulation contains sufficiently low amounts of sodium chloride and potassium chloride to reduce the saline and/or bitter taste while maintaining an effective amount of chloride, sodium, potassium, and calcium ions in the electrolyte formulation; and
wherein the electrolyte formulation has a pH ranging from about 3.9 to about 4.2.

53. The liquid electrolyte formulation of claim 52, wherein the dietary fiber is a soluble fiber, partially soluble fiber, insoluble fiber, or combination thereof.

54. The liquid electrolyte formulation of claim 52, wherein the dietary fiber is selected from the group consisting of legumes, oat bran, rye, chia, barley, fruits and fruit juices, vegetables, root tubers and root vegetables, psyllium seed, whole grains, rice, wheat and corn bran, cereals and pasta, nuts and seeds, potato skins, fruit skins, cellulose, hemicelluloses, flax seeds, lignans, psyllium husk, gum, vegetable fiber gum, and combinations thereof.

55. The liquid electrolyte formulation of claim 52, wherein the formulation increases the absorption of the sodium, potassium, and calcium ions.

56. The liquid electrolyte formulation of claim 52, wherein the formulation increases the absorption of the carbohydrates.

57. A popsicle electrolyte formulation comprising the liquid electrolyte formulation of claim 52, and about 0.06 wt % to about 0.6 wt % polysaccharide gums selected from the group consisting of sodium carboxymethyl cellulose (CMC gum), Locust Bean Gum, Guar Gum, xanthan gum, sodium alginate, carrageenan, gelatin, and combinations thereof.

58. The liquid electrolyte formulation of claim 52, further comprising about 0.7 wt % to about 20 wt % carbohydrate selected from the group consisting of dextrose, fructose, sucrose, maltose, maltodextrin, galactose, trehalose, fructo-oligosaccharides, beta-glucan, trioses, and combinations thereof.

59. The liquid electrolyte formulation of claim 52, further comprising about 0.006 wt % to about 0.06 wt % sugar substitutes selected from the group consisting of sucralose, saccharin, aspartame, acesulfame potassium, stevia, neotame and combinations thereof.

60. The liquid electrolyte formulation of claim 52, further comprising about 0.1 wt % to about 1.2 wt % preservatives selected from the group consisting of sodium benzoate, citric acid monohydrate, potassium sorbate and combinations thereof.

61. The liquid electrolyte formulation of claim 52, further comprising about 0.1 wt % to about 0.8 wt % of one or more natural and stain-free flavoring ingredients.

62. A powder electrolyte composition for reconstitution in water, comprising:
about 0.5 wt % to about 75 wt % of a dietary fiber,
about 0.6 wt % to about 6 wt % calcium chloride,
about 2 wt % to about 18 wt % sodium citrate,
about 0.4 wt % to about 4 wt % tri-potassium citrate monohydrate,
less than about 6 wt % potassium chloride, and
less than about 3 wt % sodium chloride;
wherein, upon reconstitution in water, the dietary fiber is present in sufficient amounts to increase the absorption of water by modulating intestinal activity;
wherein, upon reconstitution in water, the electrolyte formulation contains sufficiently low amounts of sodium chloride and potassium chloride to reduce the saline and/or bitter taste while maintaining an effective amount of chloride, sodium, potassium, and calcium ions in the electrolyte composition; and
wherein, upon reconstitution in water, the electrolyte composition has a pH ranging from about 3.9 to about 4.2.

63. The powder electrolyte composition of claim 62, wherein the dietary fiber is a soluble fiber, partially soluble fiber, insoluble fiber, or combination thereof.

64. The powder electrolyte composition of claim 62, wherein the dietary fiber is selected from the group consisting of legumes, oat bran, rye, chia, barley, fruits and fruit juices, vegetables, root tubers and root vegetables, psyllium seed, whole grains, rice, wheat and corn bran, cereals and pasta, nuts and seeds, potato skins, fruit skins, cellulose, hemicelluloses, flax seeds, lignans, psyllium husk, gum, vegetable fiber gum, and combinations thereof.

65. The powder electrolyte composition of claim 62, wherein the composition increases the absorption of the sodium, potassium, and calcium ions.

66. The powder electrolyte composition of claim 62, further comprising about 30 wt % to about 87 wt % carbohydrate selected from the group consisting of dextrose, fructose, sucrose, maltose, maltodextrin, galactose, trehalose, fructo-oligosaccharides, beta-glucan, trioses, and combinations thereof.

67. The powder electrolyte composition of claim 62, further comprising about 0.15 wt % to about 1 wt % sugar substitutes selected from the group consisting of sucralose, saccharin, aspartame, acesulfame potassium, stevia, neotame and combinations thereof.

68. The powder electrolyte composition of claim 62, further comprising about 2.8 wt % to about 23 wt % preservatives selected from the group consisting of sodium benzoate, citric acid monohydrate, potassium sorbate and combinations thereof.

69. The powder electrolyte composition of claim 62, further comprising about 1 wt % to about 14 wt % of one or more dry flavoring ingredients.

70. A tablet electrolyte composition for reconstitution in water, comprising:
about 0.5 wt % to about 75 wt % of a dietary fiber,
about 0.1 to about 8 wt % tri-calcium citrate,
about 2 wt % to about 18 wt % sodium citrate,
about 0.4 wt % to about 4 wt % tri-potassium citrate monohydrate,
less than about 6 wt % potassium chloride, and
less than about 3 wt % sodium chloride;
wherein, upon reconstitution in water, the dietary fiber is present in sufficient amounts to increase the absorption of water by modulating intestinal activity;
wherein, upon reconstitution in water, the electrolyte composition contains sufficiently low amounts of sodium chloride and potassium chloride to reduce the saline and/or bitter taste while maintaining an effective amount of chloride, sodium, potassium, and calcium ions in the electrolyte composition; and wherein, upon reconstitution in water, the electrolyte composition has a pH ranging from about 3.9 to about 4.2.

71. The tablet electrolyte composition of claim 70, wherein the dietary fiber is a soluble fiber, partially soluble fiber, insoluble fiber, or combination thereof.

72. The tablet electrolyte composition of claim 70, wherein the dietary fiber is selected from the group consisting of legumes, oat bran, rye, chia, barley, fruits and fruit juices, vegetables, root tubers and root vegetables, psyllium seed, whole grains, rice, wheat and corn bran, cereals and pasta, nuts and seeds, potato skins, fruit skins, cellulose, hemicelluloses, flax seeds, lignans, psyllium husk, gum, vegetable fiber gum, and combinations thereof.

73. The tablet electrolyte composition of claim 70, wherein the composition increases the absorption of the sodium, potassium, and calcium ions.

74. The tablet electrolyte composition of claim 70, further comprising about 30 wt % to about 87 wt % carbohydrate selected from the group consisting of dextrose, fructose, sucrose, maltose, maltodextrin, galactose, trehalose, fructo-oligosaccharides, beta-glucan, trioses, and combinations thereof.

75. The tablet electrolyte composition of claim 70, further comprising about 0.15 wt % to about 1 wt % sugar substitutes selected from the group consisting of sucralose, saccharin, aspartame, acesulfame potassium, stevia, neotame and combinations thereof.

76. The tablet electrolyte composition of claim 70, further comprising about 2.8 wt % to about 23 wt % preservatives selected from the group consisting of sodium benzoate, citric acid monohydrate, potassium sorbate and combinations thereof.

77. The tablet electrolyte composition of claim 70, further comprising about 0.1 wt % to about 10 wt % sucrose ester.

78. The tablet electrolyte composition of claim 70, further comprising about 1 wt % to about 14 wt % of one or more dry flavoring ingredient.

79. The tablet electrolyte composition of claim 70, wherein the tablet is chewable.

80. A beverage prepared by reconstituting in water the tablet electrolyte composition of claim 70.

* * * * *